(12) United States Patent
Saalasti et al.

(10) Patent No.: US 10,765,328 B2
(45) Date of Patent: *Sep. 8, 2020

(54) METHOD AND SYSTEM TO DETERMINE ANAEROBIC THRESHOLD OF A PERSON NON-INVASIVELY FROM FREELY PERFORMED EXERCISE AND TO PROVIDE FEEDBACK ON TRAINING INTENSITY

(71) Applicant: Firstbeat Analytics Oy, Jyväskylä (FI)

(72) Inventors: Sami Saalasti, Jyväskylä (FI); Kaisa Hämäläinen, Jyväskylä (FI); Tero Myllymäki, Jyväskylä (FI)

(73) Assignee: Firstbeat Analytics Oy, Jyväskylä (FI)

( * ) Notice: Subject to any disclaimer, the term of this patent is extended or adjusted under 35 U.S.C. 154(b) by 394 days.

This patent is subject to a terminal disclaimer.

(21) Appl. No.: 15/086,337

(22) Filed: Mar. 31, 2016

(65) Prior Publication Data

US 2017/0049334 A1 Feb. 23, 2017

Related U.S. Application Data

(63) Continuation-in-part of application No. 14/829,265, filed on Aug. 18, 2015, now Pat. No. 9,517,028.

(51) Int. Cl.
*A61B 5/02* (2006.01)
*A61B 5/024* (2006.01)
(Continued)

(52) U.S. Cl.
CPC .......... *A61B 5/024* (2013.01); *A61B 5/0205* (2013.01); *A61B 5/02405* (2013.01);
(Continued)

(58) Field of Classification Search
CPC ......... A61B 5/222; A61B 5/742; A61B 5/486; A61B 5/0205; A61B 5/7275; A61B 5/7264; A61B 5/7225; A61B 5/024
See application file for complete search history.

(56) References Cited

U.S. PATENT DOCUMENTS 6,450,967 B1 * 9/2002 Wu .................. A61B 5/222
600/485
8,858,453 B2 * 10/2014 Asukai ............. A63B 24/0021
600/500

(Continued)

*Primary Examiner* — Christian Jang
(74) *Attorney, Agent, or Firm* — Maier & Maier, PLLC

(57) ABSTRACT

A method and system for determining anaerobic threshold intensity (AnT) of a user in a freely performed physical exercise. A physiological response of a user is measured by heart rate and measured heart rate values are recorded as heart rate data. An external workload values are recorded and are each associated with one measured heart rate values to form a plurality of data points. The data points are filtered to form accepted data points, which are classified within a plurality of heart rate segments representing a heart rate within an anaerobic threshold (AnT) of the user. A data point with highest probability is stored for each segment. A first probability factor for each accepted data point is calculated. The calculated first probability factor is compared to a stored probability factor in each segment, and the higher probability factor is retained. AnT is calculated using the stored probabilities in each segment.

30 Claims, 12 Drawing Sheets

(51) Int. Cl.
    *A61B 5/22*     (2006.01)
    *A61B 5/0205*     (2006.01)
    *A61B 5/00*     (2006.01)
    *G16H 50/30*     (2018.01)
    *A61B 5/0488*     (2006.01)
    *A61B 5/083*     (2006.01)

(52) U.S. Cl.
    CPC .......... *A61B 5/0488* (2013.01); *A61B 5/0833* (2013.01); *A61B 5/222* (2013.01); *A61B 5/486* (2013.01); *A61B 5/4866* (2013.01); *A61B 5/7221* (2013.01); *A61B 5/7225* (2013.01); *A61B 5/7239* (2013.01); *A61B 5/7264* (2013.01); *A61B 5/742* (2013.01); *G16H 50/30* (2018.01); *A61B 5/7275* (2013.01); *A61B 2503/10* (2013.01)

(56) References Cited

U.S. PATENT DOCUMENTS

| | | | |
|---|---|---|---|
| 2001/0027266 A1* | 10/2001 | Hautala | A61B 5/222 600/16 |
| 2005/0164832 A1* | 7/2005 | Maschke | A63B 69/0028 482/8 |
| 2011/0040193 A1* | 2/2011 | Seppanen | A61B 5/222 600/481 |

* cited by examiner

METHOD AND SYSTEM TO DETERMINE ANAEROBIC THRESHOLD OF A PERSON NON-INVASIVELY FROM FREELY PERFORMED EXERCISE AND TO PROVIDE FEEDBACK ON TRAINING INTENSITY

FIELD

The disclosure may relate to an improved method and system for determining a person's anaerobic threshold intensity (AnT) from freely performed exercise and to provide feedback.

BACKGROUND

In order to individualize training intensity according to cardiovascular and metabolic stress exercise stress), rather than absolute external workload, different methods for determining exercise intensity have been used. These methods have been, for example, based on % HRmax, % VO2max, % HRreserve (% HRR) or % VO2reserve (% VO2R). In addition, intensity zones that are based on metabolic thresholds have been used. Lactate threshold (LT) and Anaerobic threshold (AnT) (or onset of blood lactate accumulation OBLA) are such metabolic thresholds corresponding to a lactate threshold of about 2.5 mmol/l and 4.0 mmol/l, respectively. Training zones have been divided between these thresholds: 1) "Basic endurance training" or "long slow distance" below LT, including all steady pace exercises in which lactate is below 2.0 or 2.5 mmol/l level; 2) "Threshold training" between LT and AnT including steady pace and interval training with lactate values between 2.5 and 4.0 mmol/l; 3) VO2max training above AnT with lactate values over 4.0 mmol/l. As would be understood by a person of ordinary skill in the art, other intensity zone models have been applied in training. They may be informative in training practice, but it is important to note that they are not based on clearly defined physiological markers.

AnT may be metabolically characterized as the highest workload at which the body is able to achieve steady-state condition, which means that the lactate (specifically lactic acid) accumulation and removal (by metabolizing) is in balance so that lactate level stays stable. For example, if a person's AnT pace for running is 4:00 min/km, the person is able to run with that speed with a constant lactate level of about 4 mmol/l for prolonged periods. If the person increases pace to, for example 3:50 min/km, he/she may no longer able to achieve a steady state. Instead the person's lactate level may accumulate from an approximate 4 mmol/l starting level up to 10 mmol/l or higher until subjective fatigue takes place. Further, AnT may not be an exact lactate level but may vary between individuals. Lactate level corresponding to AnT may usually be between 3.0 and 4.0 mmol/l and may depend, for example, on personal physiological characteristics, or other factors as would be understood by a person of ordinary skill in the art.

Despite small individual variation in lactate levels corresponding to AnT, the same or similar physiological reactions may be related to it. For example, when exercise intensity is increased gradually from rest, at certain points anaerobic energy pathways usually start to noticeably activate and support the aerobic energy system in producing energy, which may sustain the energy demands of the body in the form of ATP. When anaerobic energy pathways are activated, glycogen/glucose can be used more rapidly to form ATP through glycolysis. This may result in fast lactate formation in the muscles. Until AnT, the lactate can be metabolized by the body without continuous accumulation. If exercise intensity is increased above AnT, aerobic energy production capabilities of the working muscles may have difficulties in matching the exercise energy requirements, and anaerobic energy production may increase rapidly. Consequently, lactic acid (lactate) may start to accumulate into the muscles and blood stream. When exercise intensity exceeds AnT, accumulation of lactic acid in muscles may cause fatigue in a brief period of time.

As would be understood by a person of ordinary skill in the art, similar terms may refer to the same physiological phenomenon as AnT. Non-limiting examples may include onset of blood lactate accumulation (OBLA), maximal lactate steady-state (MLSS), and respiratory compensation thresholds. All of these may refer practically to the same exercise intensity where lactic acid starts to accumulate due to the body's inability to remove lactic acid by oxidation and glucose re-formation(gluconeogenesis). This may cause a reduction in blood bicarbonate levels because bicarbonate can buffer the rise in acidity. Consequently, the body's carbon dioxide ($CO_2$) production may be increased, thus possibly leading to increased $CO_2$ removal from the body by means of increased respiration rate and ventilation. This rapid increase in ventilatory parameters can be used to detect these thresholds when exercise intensity is increased incrementally (for example, in test situations). Another detectable sign in incremental exercise tests may be the deflection point of heart rate. That is, at low to moderate intensities heart rate may increase linearly in relation to external work performed (e.g. speed or watts), but at AnT intensity, the increase in heart rate may start to slow. To clarify, this kind of metabolic threshold can be determined for everyone, whether one is sedentary, highly trained, or otherwise, but the exact lactate level may vary depending on individual physiological characteristics, for example between 3-4 mmol/l. Regardless of the exact lactate value, the same or similar physiologic responses may occur and these responses are measured in order to determine the threshold intensity. Heart rate level and/or pace (e.g. min/km or km/h) corresponding to AnT may be relevant training parameters since either one or both can be measured during any exercise and the user can easily observe whether he/she is on the right intensity zone or not. Pace (e.g. min/km or km/h) corresponding to AnT may allow an individual to, for example, track changes in fitness level because AnT-pace is a relevant predictor of, for example, marathon performance. Alternatively, other training parameters can be measured as would be understood by a person of ordinary skill in the art.

Accordingly. AnT may present an exercise intensity level that is important to long-term performances as it may represent the highest intensity of performance that can be tolerated for relatively long periods. The metabolic characteristics of AnT (and other similar lactate derived threshold values such as OBLA and MLSS) may be related to those of critical power, which is a concept that aims to represent the highest workload at which it is possible to perform, for example, 30 min to 60 min all-out time trials. In practice, the intensity may be higher at critical power than at AnT, and the AnT has been associated with a lower workload and increased time to exhaustion when compared to critical power.

Downsides of the current methodologies to define AnT are well known. The available methods for estimating the AnT require specific exercise protocols with incremental exercise intensity. Moreover, laboratory tests are invasive since blood lactate samples are used to determine AnT. Further, a single incremental test might not be accurate in each case, as there is variation in the individuals' performance level from day to day. Additionally, laboratory tests can cause anticipation and be stressful, which may affect physiology and the accuracy of the results. Therefore, it would be very beneficial if anaerobic threshold could be non-invasively analyzed from day to day with freely performed real-life exercises outside of laboratory conditions. This may be easier for the users, and as more data on determined anaerobic threshold may become available, it may also increase accuracy and reliability of the determined anaerobic threshold value.

SUMMARY

Exemplary embodiments of the disclosure may determine a person's anaerobic threshold intensity from, for example, freely performed exercise, and may further provide feedback.

In one exemplary embodiment, a method for determining a person's anaerobic threshold intensity (AnT) in a freely performed physical exercise may be conducted according to the following exemplary steps:

a. the user may start to perform an exercise;
b. physiological response may be continuously measured by heart rate, and measured heart rate values may be recorded with time stamp as heart rate data;
c. external workload may be continuously measured, and measured workload values may be recorded and associated with recorded heart rate values, and each heart rate value and associate workload value may form a data point;
d. unreliable data points may be filtered using predetermined criteria, and remaining points may form accepted data points;
e. accepted data points may be classified to selected narrow segments regarding heart rate covering AnT, including segments below and above a probable heart rate value of AnT, and at least one data point in each segment may be stored in records;
f. a first factor P1[i] may be calculated for probability for each accepted data point based on external workload and heart rate variability, wherein factor P1[i] may be part of total probability P[i] which may depict a likelihood of AnT being in respective segment [i].
g. the calculated probability factor P1 may be compared with a previous value in a respective segment, and if higher, the respective data point may be updated in the record, and if otherwise, it may then be disregarded; and
h. when requested, continuing to a full calculation, wherein
i. executing the full calculation of the estimate of AnT may include calculating optional remaining (P2, P3) factors for each total probability P[i], the full calculation using the stored data of the said records; and
j. calculating an estimate of AnT as a weighted value of all heart rates of each segment and each total probability P[i] therein.

In another exemplary embodiment the overall probability may be split to factors (P1, P2 . . . ). The major part of total probability (P1) may be chosen so that the need of calculation may be minimized, but full calculation can be executed whenever AnT should be given to the user. Full calculation may use segmented data as a base. In that exemplary embodiment, candidates may be calculated into segments, and updating remaining parts (P2, P3) may take place rarely. The segment data may include, for example, elapsed time, heart rate, external workload (e.g. theoretical oxygen consumption, watts or speed (v)), maximum external workload during the exercise (e.g. maximum speed ($v_{max}$)), mean average MN (MAD), minimum MAD (MADmin), or other data as would be understood by a person of ordinary skill in the art.

In another exemplary embodiment, the major part (P1) of total probability (P) may be calculated, for example, based on the relationship between current external workload and highest measured external workload, and the relationship between current and lowest measured heart rate variability level.

In another exemplary embodiment, remaining factors (P2,P3) may at least be based on a user's fitness level and population reference values, the population reference values being related to the normal location on AnT in HR-scale, as would be understood by a person of ordinary skill in the art. In one example, it may be about 90% of HRmax, but could be any similar value without departing from the scope of the disclosure. In some embodiments, a population reference value may be based, for example, on linear dependency between heart rate and external workload.

In other exemplary embodiments, intensity level corresponding to a best estimate of the user's anaerobic threshold is determined. Determined intensity level corresponding to a user's anaerobic threshold can be expressed as an absolute or relative value describing intensity, for example, heart rate (HR) level, percentage of maximal intensity (% HRmax, % VO2max, % METmax), pace (min/km or min/mile), speed (km/h or mph), theoretical VO2 (ml/kg/min) or any other parameter describing exercise intensity.

In another exemplary embodiment, the user may be advised through the feedback regarding an aim of the exercise, and/or the user may be advised by the feedback to, for example, choose an exercise type from a preset group of different exercise types.

Anaerobic threshold estimate can be given during and/or after exercise to the user, or to any external system.

The method could be implemented in any device comprising a processor, memory and software stored therein and a user interface, for example, a heart rate monitor, fitness device, mobile phone, PDA device, wristop computer, personal computer, and the like.

The following Table 1 may show exemplary definitions and abbreviations of terms used in the exemplary embodiments described herein.

TABLE 1

Exemplary Definitions and Abbreviations

| Term or abbreviation | Definition |
| --- | --- |
| AnT | Anaerobic threshold. Refers to the highest velocity or external power output that a person's can maintain during physical activity without continuous lactic acid accumulation. |
| HR | Heart rate (beats/min) |
| HRmax | maximum heart rate (of a person) (beats/min) |
| % HRmax or phr | heart rate relative to maximum heart rate |
| VO2 | Oxygen consumption (ml/kg/min) |
| VO2max | maximum oxygen consumption capacity of a person (ml/kg/min) |
| % VO2max | measured VO2 relative to VO2max of a person |
| % VO2R | (measured VO2-resting VO2)/(VO2max-resting VO2) |

TABLE 1-continued

Exemplary Definitions and Abbreviations

| Term or abbreviation | Definition |
|---|---|
| Theoretical VO2 or theoretical oxygen consumption | Value that describes external workload (ml/kg/min). Can be calculated based on speed and altitude change (or speed and grade of inclination), or based on measured power output in bicycles and other exercise equipment. |
| METmax/maxMET/ maximal_MET | maximum oxygen uptake capacity of a person relative to resting oxygen consumption = VO2max (ml/kg/min)/resting VO2 (ml/kg/min) = VO2max (ml/kg/min)/3.5 ml/kg/min |
| v | In this application may refer EITHER to actual velocity measured during physical activity OR to a calculatory level-ground running velocity that has been converted from measured power output (watts) or measured running speed at any grade of inclination (for example product of measured running speed and measured altitude change). |
| v_max or vmax | In this application may refer EITHER to actual maximum velocity measured during physical activity OR to a calculatory maximal level-ground running velocity that has been converted from measured power output (watts) or measured running speed at any grade of inclination (for example product of measured running speed and measured altitude change). |
| R-R-interval | Time interval between successive heart beats |
| HRV | Heart rate variability meaning the variation in time interval between successive heart beats. The magnitude of heart rate variability may be calculated from electrocardiographic or photoplethysmographic signals, for example. |
| MAD | Mean absolute difference of successive heartbeat intervals. Typically refers to a measured HRV level. |
| MADmn or minMAD or MADmin | Typically refers to the lowest HRV value that has been measured during ongoing exercise. |
| Heart rate segment | Accepted (=reliable) data points in AnT estimation may be classified to selected narrow segments regarding heart rate covering AnT. There may be one or more segments below and one or more segments above expected AnT. For example, eight successive segments can be used between 79-95% HRmax or 80-96% HRmax. Accordingly, the intensity range of each segment can be 2% HRmax, for example. |
| Freely performed physical exercise | An exercise that may be performed without a specific protocol. The user may freely decide the intensity of exercise, as well as recovery periods inside the exercise session. |
| Continuous measurement | Continuous measurement of heart rate or external workload during exercise may include any type of measurement that is done through the whole exercise. Continuous measurement may also refer to measurements that are done intermittently throughout the exercise: All data can be recorded but it is also possible to record for example 1 minute of data after every 3 min of exercise (for example 0-1 min recording, 1-3 min not recording, 3-4 min recording, 4-6 min not recording . . . ) |
| P1-P3 . . . Pi | Probability factors that are used to calculate the total probability of AnT at each heart rate segment |
| EPOC | Excess post-exercise oxygen consumption. As it can be nowadays estimated or predicted - based on heart rate or other intensity derivable parameter - it can be used as an cumulative measure of training load in athletic training and physical activity. |
| Critical power or critical velocity or critical speed | A level of power output or velocity that can be maintained for relatively long periods. At critical power (velocity) exhaustion may occur after 20-40 min of exercise. Critical power (or critical velocity) correlates with AnT. |

BRIEF DESCRIPTION OF THE FIGURES

Advantages of embodiments of the present disclosure will be apparent from the following detailed description of the exemplary embodiments. The following detailed description should be considered in conjunction with the accompanying figures in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Further, many of the embodiments described herein are described in terms of sequences of actions to be performed by, for example, elements of a computing device. It should be recognized by those skilled in the art that the various sequences of actions described herein can be performed by specific circuits (e.g. application specific integrated circuits (ASICs)) and/or by program instructions executed by at least one processor. Additionally, the sequence of actions described herein can be embodied entirely within any form of computer-readable storage medium such that execution of the sequence of actions enables at least one processor to perform the functionality described herein. Furthermore, the sequence of actions described herein can be embodied in a combination of hardware and software. Thus, the various aspects of the present invention may be embodied in a number of different forms, all of which have been contemplated to be within the scope of the claimed subject matter. In addition, for each of the embodiments described herein, the corresponding form of any such embodiment may be described herein as, for example, "a computer configured to" perform the described action.

Figure 1:
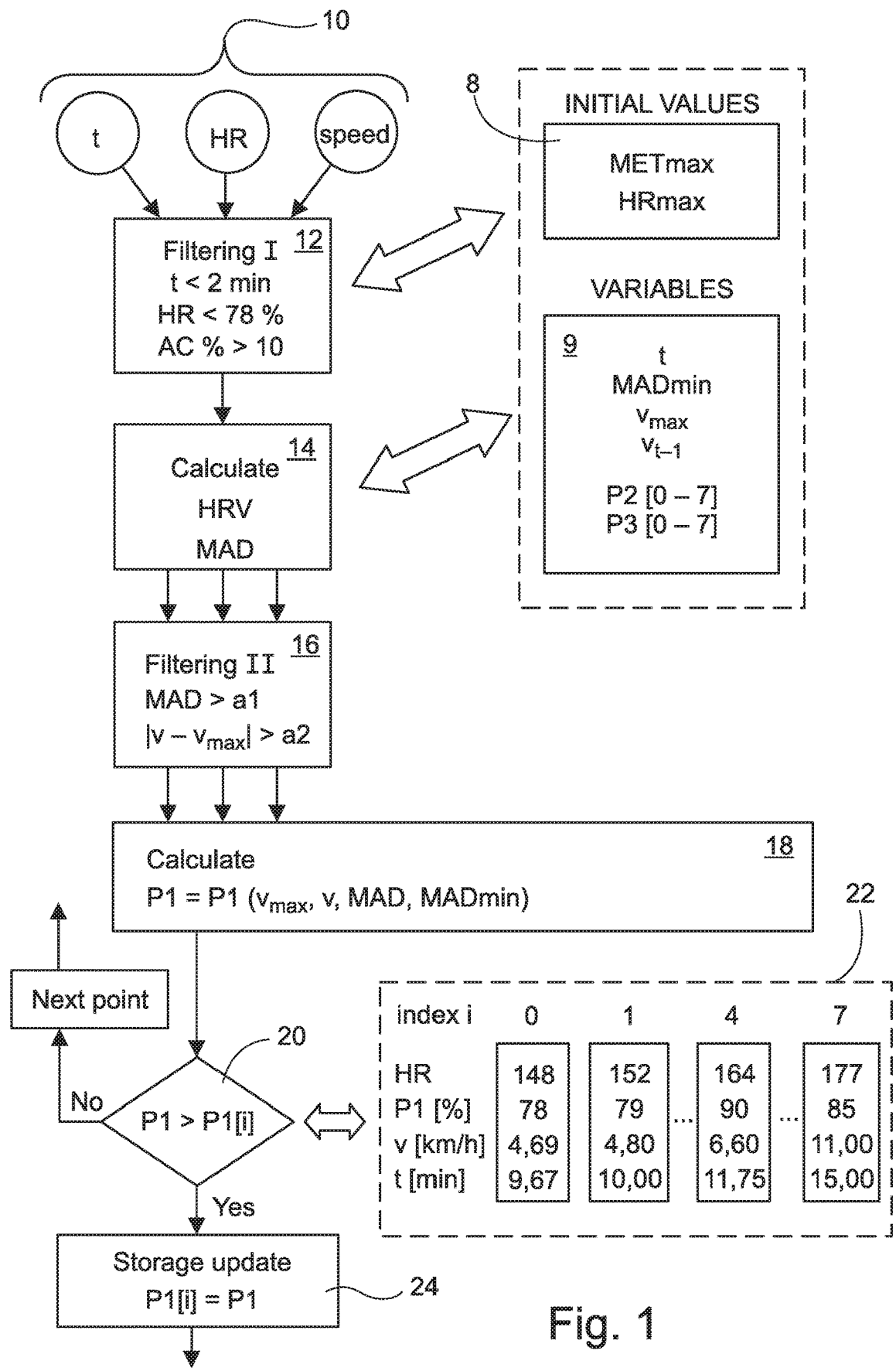
FIG. 1 presents an exemplary flowchart illustrating an implementation in an exemplary digital device.
Figure 2:
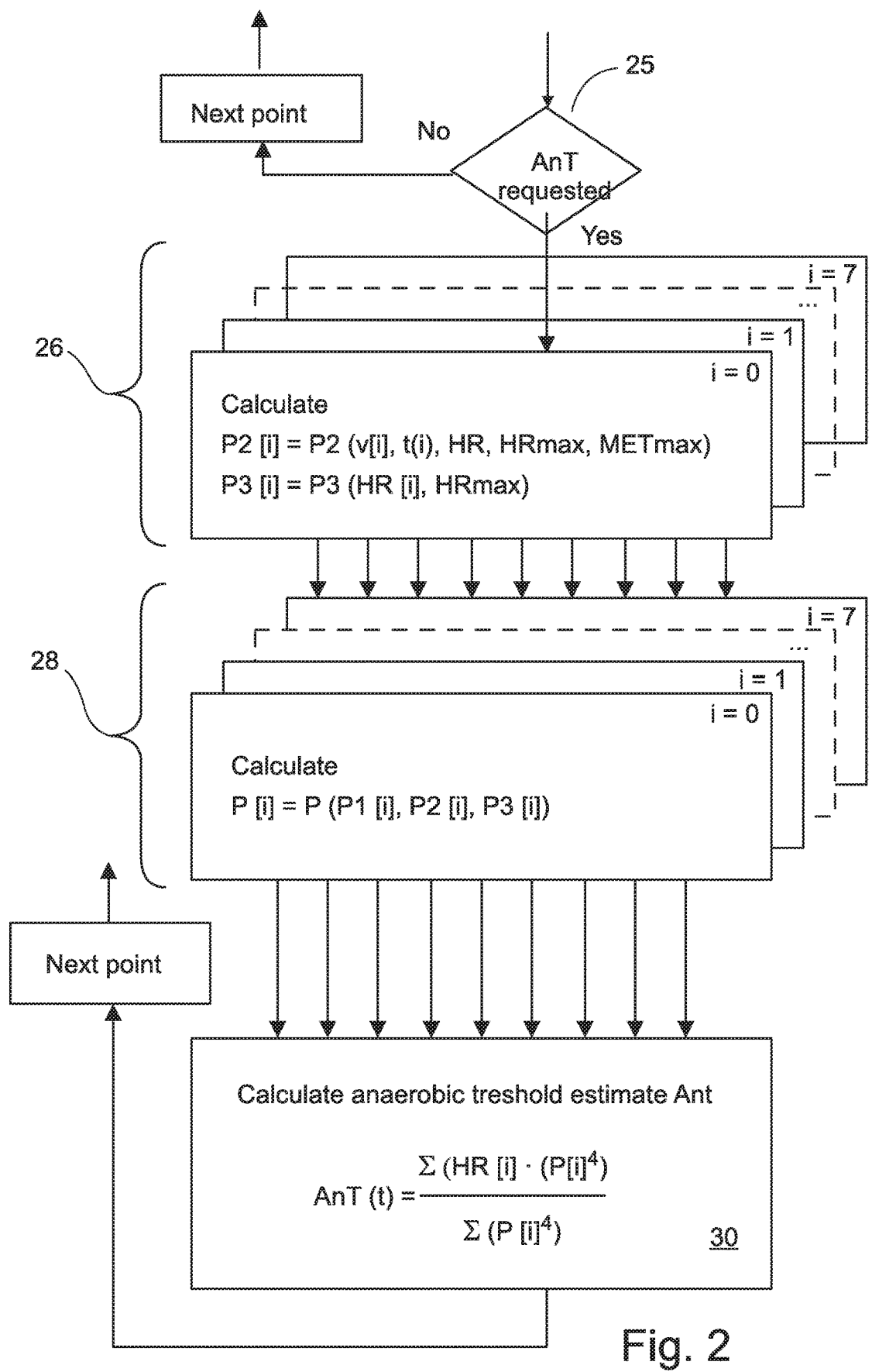
FIG. 2 is a continuation of FIG. 1 and presents an exemplary flowchart illustrating the implementation in the exemplary digital device.

The method can be implemented in versatile devices, which have resources for measuring internal intensity and external workload, and run software to execute processes depicted in the exemplary flowcharts of FIGS. 1 and 2. A schematic hardware assembly is depicted below in exemplary FIG. 11.

Initial background and personal data may be stored. For example, the performance level (for example VO2max or METmax) and the maximum heart rate (HRmax), and the like, of the user may be stored. Personal data may be entered or determined beforehand.

In one exemplary embodiment, AnT may be determined as shown in exemplary FIGS. 1-2. At step (10) the digital device may continuously monitor heart rate (HR) and speed of a user. Time (t) may be monitored internally by, for example, a central processing unit (CPU) of the device. The raw data may be filtered initially using chosen threshold values (12) for elapsed time, heart rate, heart rate variability or other value. The external work data may also be filtered using, for example, one or more artifact criteria.

In step (14) heart rate variability (HRV) values, for example, MAD (mean absolute difference), may be calculated and stored. The data point may be filtered out at step (16) if, for example, the MAD value is too high, or speed is not stable.

Further exemplary embodiments may include easy filtering phases, a calculation of characterizing probability value P1 for a certain HR-segment, and a determination if more complex calculation is needed, whereby a full calculation may be executed only in a chosen situation. At step (20), when the calculation of P1 takes place, the segment (i) data corresponding to the actual measured heart rate may be determined. This data may contain values of the exact heart rate HR[i], probability P1, registered speed (v), registered time, and the like. At step (24), an index register is updated when new value P1 is better than a corresponding value P1[i] in the segment record (22) of a respective heart rate range. The segment records (22) may have the fields for best data point in each segment, for example, heart rate, calculated probability P1, speed (v), time, and the like.

In one embodiment the new probability factor is not just replacing the old one, but the factor is updated with new value, eg.

updated value to be stored=0.5×new value+0.5×old value

In another exemplary embodiment p-value is taken into account in updating:

updated value to be stored=$p1$×new value+$((1-p1)$× old value)

In still another exemplary embodiment p-value is taken into account in updating in following way:

($p1\_new$×$HR\_new$)+($p1\_previous$×$HR\_previous$)/ ($p1\_new$+$p1\_previous$).

At step (18), the probability P1 may be calculated, for example, using variables speed (v), maximum speed ($v_{max}$), mean average HRV (MAD), minimum MAD (MADmin), and the like.

At step (25), after index registers (20) are updated, a request of AnT may exist, and if so, at step (26), probability factors, for example P2 and P3, may be calculated. If AnT is not requested, the execution may return to check a next data point.

In some exemplary embodiments, probability P2 may be calculated as a negative part in total probability based on, for example, how much change in external workload deviates from expected change in external workload, or other factors as would be understood by a person of ordinary skill in the art. Expected change (segment (i) and segment (i−1)) in external workload may be calculated based on change in heart rate between values in respective segments. Expected change in external workload may be calculated based on METmax. The change may be calculated in values between a chosen segment (i) and any segment with lower index.

In further exemplary embodiments, probability P3 may be based on, for example, expected value of 90% of maximum heart rate that is known as a population reference value for AnT, but could be based on alternative measurements as would be understood by a person of ordinary skill in the art. Because it is possible that fit individuals may have higher (and sedentary individuals lower) AnT than 90% of maximum heart rate, it is obvious that an adaptive reference value may be used instead of fixed 90% value.

At step (28), total probability (P) for a recorded HR in each segment (i) may then be calculated through P1, P2 and P3.

In other words, P[i]=P(P1[i], P2[i], P3[i]).

For example P[i]=(P1[i]+P2[i]+P3[i])$^z$, where z=1 . . . 6. The power '6' gives a strong filtering of small probabilities.

Finally, at step (30) an estimate of anaerobic threshold (AnT) may be calculated as a weighted value from all AnT candidates in all segments (i) according to the following exemplary equation.

$$AnT(t) = \frac{\sum (HR[i] * (P[i]^y)}{\sum (P[i]^y)}$$

The registered heart rate value and external workload (AnT-candidate) of each segment may be multiplied by the total probability of that segment when all weighted AnT-candidates are added together.

In the example above, the probability values $P2[i]$ and $P3[i]$ may each have a matrix with eight elements (as also P1 may have). However, the calculation may be modified such that only a limited number of registers is needed when, for example, steps (26), (28) and (30) are executed simultaneously. In some exemplary embodiments, the components of the weight function could be calculated in the index order.

Exemplary FIGS. 6-10 may illustrate relationships of major components in the probability factors P1, P2 and P3. Due to scaling of probabilities, $P[i]=((P1[i]+P3[i])/2+P2[i])^\wedge z$, When calculating weight-values, the probabilities of the segments are emphasized by a chosen power 'y'. In some exemplary embodiments, values of 'y' are 3-6, but could be any value as would be understood by a person of ordinary skill in the art. The weight function (at step 30) may use high power (here '4') for the probability $P[i]$, but then the power $z=1$ (or vice versa). This may reduce the influence of lower probabilities. However, in a case where many segments have similar probabilities, the result value may better correspond to the true physiological AnT-value this way than by picking the data point with the highest probability.

In one exemplary embodiment a user (e.g. an athlete or keep fit enthusiast) may start an exercise session. The type of exercise can be either interval or continuous. The user can freely decide the intensity of exercise, as well as recovery periods inside the exercise session. Heart beat interval data and performance data can be continuously measured (speed and altitude or power output) during the exercise using, for example, a heart rate monitor, wristop computer or other related device as would be understood by a person of ordinary skill in the art. Even a heartbeat sensor that is connected to a mobile phone or PDA device (using for example Bluetooth connection) can be used, in which case the mobile phone or PDA device would measure external workload (speed and altitude) and serve as a CPU unit. The system may continuously validate and calculate heart beat and performance data and may form an estimate of a user's anaerobic threshold (AnT). Continuous measurement of HR during exercise may include any type of measurement that is done through the whole exercise. For example, all RR-intervals measured from electrocardiographic during exercise are usually recorded, but in the case of photoplethysmographic signal it is typical that beat to beat intervals are recorded only intermittently during exercise. However, despite intermittent recording, photoplethysmographic signal can be also used.

In further exemplary embodiments the user may exercise outdoors. The user can exercise, for example, by walking or running. In some embodiments heart rate may be measured using a heart rate transmitter belt, or the like, and analyzed in a CPU-unit that can be, for example, a normal sports watch, wristop computer, or similar device as would be understood by a person of ordinary skill in the art. Alternatively, it may be possible to use ppg-signal processing so that both the measurement and analysis of data may be done using a wristop device, or the like. Measurement of speed and altitude can be done using a GPS signal. The GPS receiver may be embedded, for example, in the wristop device, but an external GPS receiver can be used as would be understood by a person of ordinary skill in the art. Altitude data can be retrieved from GPS data, additional barometer data, and the like. A barometer may be embedded in the wristop computer. In the described exemplary embodiments a user may, for example, walk or run (or both) during the exercise. The terrain can be whatever the user wants, for example, hilly or flat. During the exercise, data points may be continuously validated and calculated. The AnT estimate can be shown to the user during the exercise, or after exercise, as desired.

In some of the above described exemplary embodiments, heart beat data, speed data and altitude data may be gathered and used, for example, when the user is exercising on foot (walking/pole walking or running) outdoors. In still further exemplary embodiments, a WIFI technique, for example, may be used so that positioning can be determined indoors. It may also be possible to use an accelerometer signal (for example an accelerometer positioned on a user's foot or the like) to define walking/running speed indoors or outdoors, and that data can be used together with barometer data. It is also possible that the exercise is done using a treadmill, or the like. In that case, it is also possible that the speed data can be retrieved from an accelometry signal, or the like. In one exemplary embodiment a user can input treadmill speed data to the CPU while the heart beat data is continuously measured.

In some of the above described exemplary embodiments, a user may exercise on foot either by walking/Nordic walking, running, or the like. It is also possible to define AnT in other exercise modes, for example cycling or rowing, wherein the power output can be easily measured and retrieved. As would be understood by a person of ordinary skill in the art, power output can be measured in cycling, for example, using a power meter embedded in pedals or chains, and this power data can be shown to the user in a wristop device, or the like. In one exemplary embodiment related to cycling—speed and altitude data may be replaced with power output data measured from a bicycle. The user can do the bicycling exercise indoors or outdoors, and on any desired terrain. In some exemplary embodiments, AnT estimation may only require that both pedaling power and heart beat interval data are measured.

Referring generally to the exemplary embodiments, where power output is measured, (e.g. cycling or speed and altitude of walking or running are measured) it is possible to increase the accuracy of AnT estimate by measuring performance data. This is because heart beat data can be measured continuously as a function of performance data. In this comparison the relationship between performance data and heart rate should be linear. Data points which seem to be "outlier" points—when compared to the linear relationship—can be excluded from the AnT estimation.

An example of interaction between cycling power output and running speed may be presented below with reference to FIG. 3. On the basis of this relationship it is understood by a person skilled in art that the same or similar calculation can be used in cycling (or rowing etc.) and walk/run exercises. The power is presented as watts per user's weight (kg). It will be understood that this is only an example of this interaction in cycling using well known calculation formulas. The relationship may be similar in the case of indoor rowing, or other sports. There are some factors, for example, sport specific efficiency (economy) of movement which may cause small variations in this relationship between different sports. For example, the following calculation formulas can be used for theoretical VO2:

Theoretical VO2 of running (ml/kg/min)=0.2*(speed m/min)+0.9*(speed m/min)*TAN (grade of incline)+3.5

Theoretical VO2 of walking (ml/kg/min)=1.78*
(speed m/s)*60*(TAN(grade of incline)+0.073)

A threshold speed of e.g. 7.5 km/h can be used in switching from walking formula to running formula. Alternatively, detection between walking and running can be used using accelerometer data.

In cycling, power output can be converted to VO2 using the following exemplary formula:

Theoretical VO2 of cycling (ml/kg/min)=((power watts)*12+300))/weight

Figure 4:
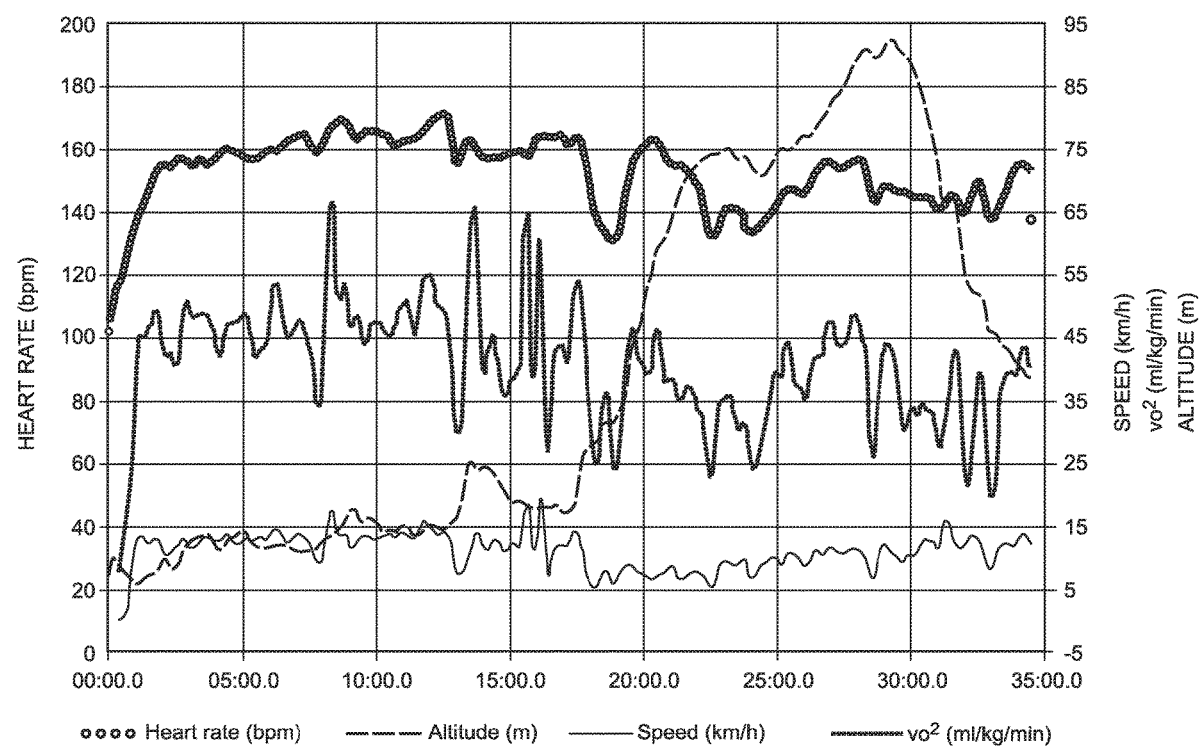
FIG. 4 presents an exemplary chart showing heart rate, speed, altitude and theoretical VO2 (calculated based on speed and altitude) collected during a normal training session.

FIG. 4 presents examples of heart rate, speed, altitude and theoretical VO2 (calculated based on speed and altitude) which may be collected during a normal training session.

Figure 5:
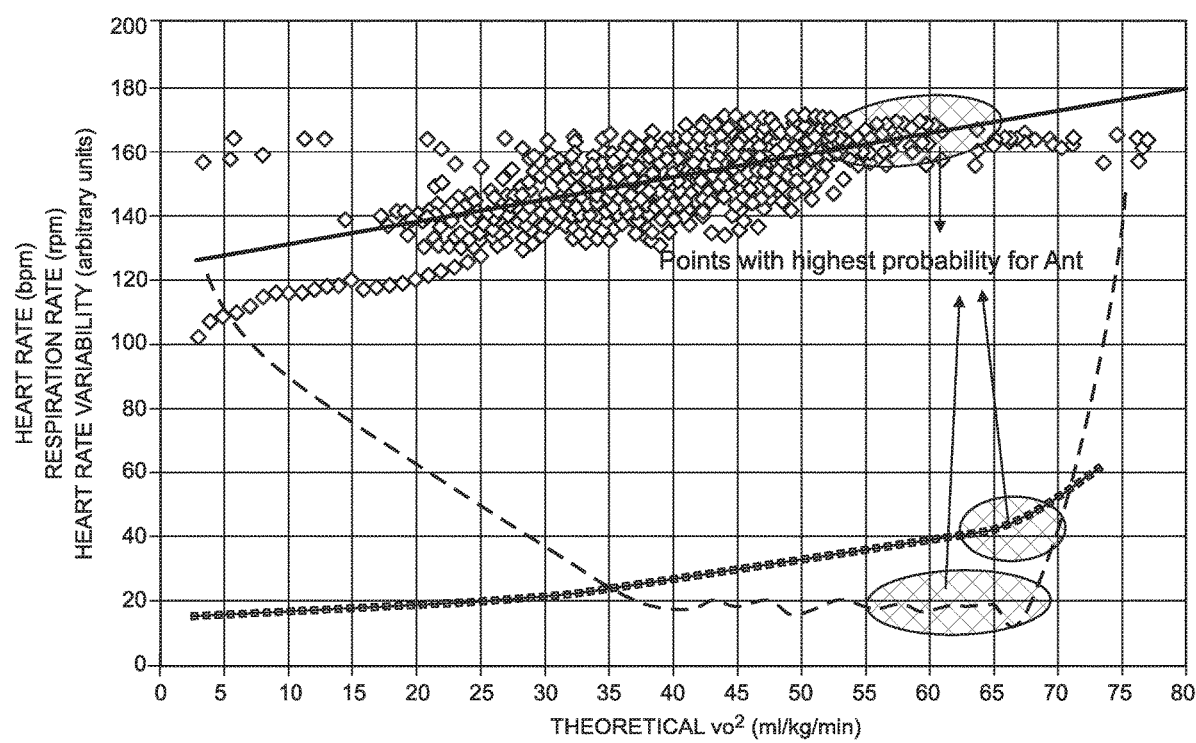
FIG. 5 presents an exemplary chart showing measured heart rate (points) and a line of best fit (solid line) as a function of external work (theoretical VO2) based on the data shown in FIG. 4, and usual pattern respiration rate (dotted line) and heart rate variability (dashed line).

FIG. 5 shows exemplary exercise (for example, running/walking) data representing heart rate, speed and altitude recorded during exercise as a function of exercise time. In addition, theoretical oxygen consumption (VO2), that may be calculated based on speed and altitude, is further shown in exemplary FIG. 5. Data presented in FIG. 5 could be derived from the same exercise that has been shown in FIG. 4. In the examples of FIG. 4 and FIG. 5, when this exercise data is observed in another perspective, for example as a function of theoretical VO2, the idea of calculation may be shown. In other words, near anaerobic threshold heart rate values often tend to show a downturn below linear dependency, heart rate variability is usually close to its minimum levels and heart rate derived respiration may start an exponential increase. These physiological markers are searched from the data.

Still referring to FIG. 5, the exemplary measured heart rate (points) and the line of best fit (solid line) may be shown as a function of external work (theoretical VO2). The dashed line may represent the heart rate variability index. As can be seen, the probability for AnT may be high, for example, when HRV index is close to its minimum value and when heart rate (points) starts a downturn compared with the linear dependency line (line of best fit). In addition, heart rate derived respiration rate can be used in AnT detection. Respiration rate (dotted line) may start to increase exponentially after AnT has been reached. In this example, respiration rate and heart rate variability lines are merely schematic examples of the phenomena.

In some exemplary embodiments, the data (for example, HR, external work, HRV, HRV-based respiration parameter) may be compartmentalized, for example, into 8 different 2% segments based on individual % HRmax. More generally there may be anywhere from 5-30 segments and the size of each segment may a be anywhere from 0.5-3%.

The system may seek to find the most probable location of AnT using the data from these segments that can locate, for example, within approximately 79-96% of individual HRmax (at least 7% difference between the low end and the high end may be required, e.g. 89-96% of HRmax). There can be similar kinds of restrictions for HRV and external work, as would be understood by a person of ordinary skill in the art.

Within each segment, a suitable data point to represent that specific segment may be chosen from all data candidates according to, for example, quality metrics of the data, fuzzy logics and without using thresholds.

The possibility for a suitable data point to be chosen may increase, for example, when heart rate variability is at a low level, and may be highest when HRV is the lowest possible within segment.

The possibility for a suitable data point to be chosen may increase, for example, when external workload (e.g. speed or theoretical VO2 or power output) is high, and when external workload is stable.

The data points may be evenly distributed over the exercise.

The system may assume that the data for lower external work are taken from an early part of the exercise, if available, and the data for higher external work are taken from the later part of the exercise, if available.

Probabilities (P1-P3) of each of the chosen data points to be the AnT-estimate may be calculated. For example, in the case of P2 calculation, heart rate from the chosen data points may be compared to external work, and linear increase may be expected for heart rate when external workload increases (as shown in FIG. 5). As an example of P2, outlier points may have lower probability-value. Above AnT intensity, a downturn of heart rate may occur causing these measurement points to deviate from a linear regression line, thus possibly leading to lower P2 values.

If the data point representing a high intensity segment is timely located significantly later than any or some other chosen data points, and does not show significant decrease in the heart rate vs. speed relationship, the probability of that point or higher intensity data point to be the AnT may be increased (P2-probability increases).

In some exemplary embodiments, approximately 90% of HRmax may be used as a population level reference, and the probability of the data point to be defined as AnT may be increased when locating closer to that reference (P3-probability increases).

In still other exemplary embodiments, a heart rate variability (HRV) measure may be used in the AnT determination. Heart rate variability may be high at low intensities and may start to decrease when exercise intensity rises to a moderate level, for example, over 60% of maximal heart rate. Between about 60-80% heart rate variability may be considered a low level. The point at which variability starts to increase again, for example, between 85 and 90%, may be close to AnT. This is because the acidity induced sudden increase in ventilation may cause increased variability in heart rate (differences in successive heart beat intervals). Data points located close to "HRV increase" may have a high AnT probability (P1-probability increases).

Attributes of the data points (HR, external work, P1, t, and the like) may be stored.

By using probabilities calculated for each segment, AnT may be calculated as, for example, a weighted sum from all segments.

AnT can be provided for the user or other system in real-time or after the exercise, as desired.

If data points do not appear to include AnT, extrapolation of the data can be used to specify the most probable AnT location as % HRmax or HR level. Extrapolation can be made based on the slope-value of heart rate as a function of external workload in the highest segment with stored heart rate. In the case that slope value is high when exercise highest measured heart rate is reached, say at 87% HRmax, it may be concluded that AnT locates at 92%, for example. On the other hand, the same example in perspective, if the slope-value would have been low it could be concluded that AnT locates at 87%. Slope-value expresses the relationship between change in heart rate and external workload calculated from values in respective segments. The extrapolation of AnT-value is based on empiric model or function.

Another embodiment may require for giving AnT estimate that a user reaches a certain heart rate limit during exercise that may be 90% of maximum heart rate, for example.

The accuracy of the method may increase when more data is collected for a specific user by learning from the user data.

The method and the system can be used in any type of exercise where and external work can be measured, as would be understood by a person of ordinary skill in the art.

Further exemplary embodiments for the calculation of previously described probabilities are described below. In one exemplary embodiment, three probability factors P1-P3 may be used, although more probability factors may be used as desired. AnT may be determined as a weighted average of these probabilities.

Figure 3:
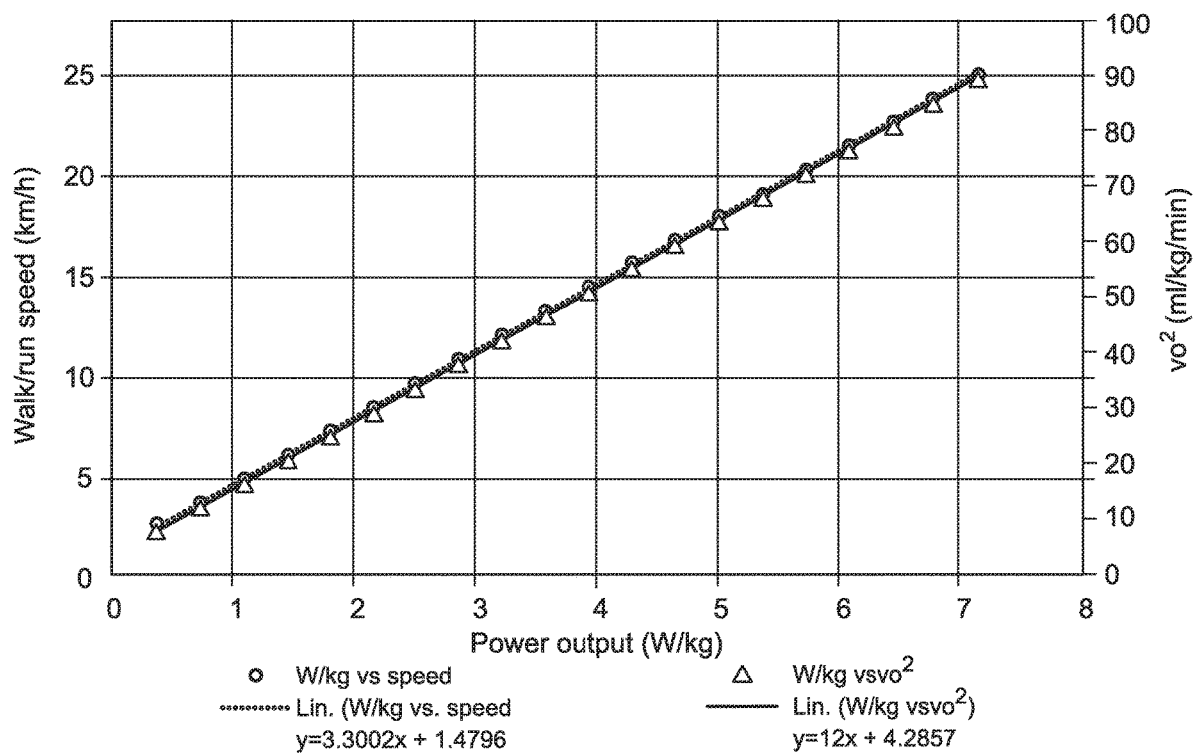
FIG. 3 presents an exemplary chart of interaction between cycling power output, running speed and theoretical oxygen consumption.

In some exemplary embodiments, the mathematical formula for P1 may be expressed as Matlab® M-code:

$$P1=(1500-100*(vmax-v)-600*(MAD-MADmin))/15,$$

wherein v=current speed (km/h; watts from e.g. cycling can be transformed to km/h scale if needed according to FIG. 3), vmax=highest measured speed, MAD=current HRV-level, MADmin=lowest measured HRV-level.

If a current P1 value is lower than a P1 value already measured for that HR segment [i], then the P1 current value may be rejected. Otherwise, the current P1 value may be recorded as one AnT candidate (HR, v, P1, t), where t is a current time moment.

Figure 6:
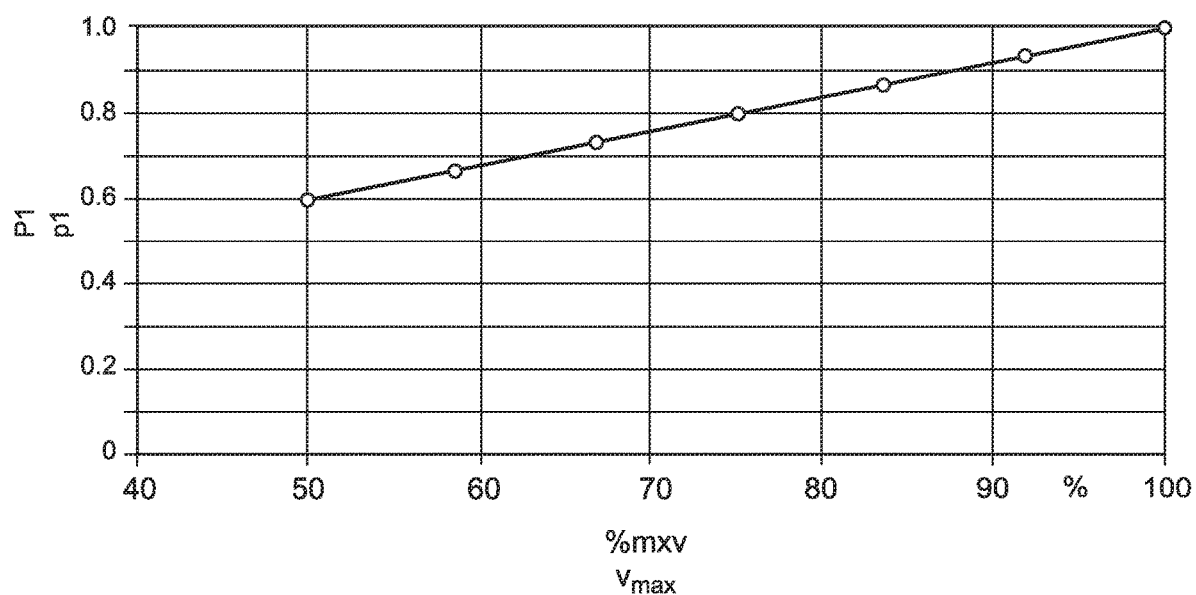
FIG. 6 presents an exemplary chart showing the effect of current intensity (as a percentage of a session's highest speed) on P1 value when current MAD value remains constant.

The idea of this P1 calculation is that a higher current speed (relative to highest speed measured during exercise) may result in a higher P1 value, because increasing or steady state intensities may be more reliable for determining AnT as compared with decreasing intensity. FIG. 6 shows an example of the effect that current speed (as a percentage of session's highest speed) may have on P1 value when current MAD value is constant.

Figure 7:
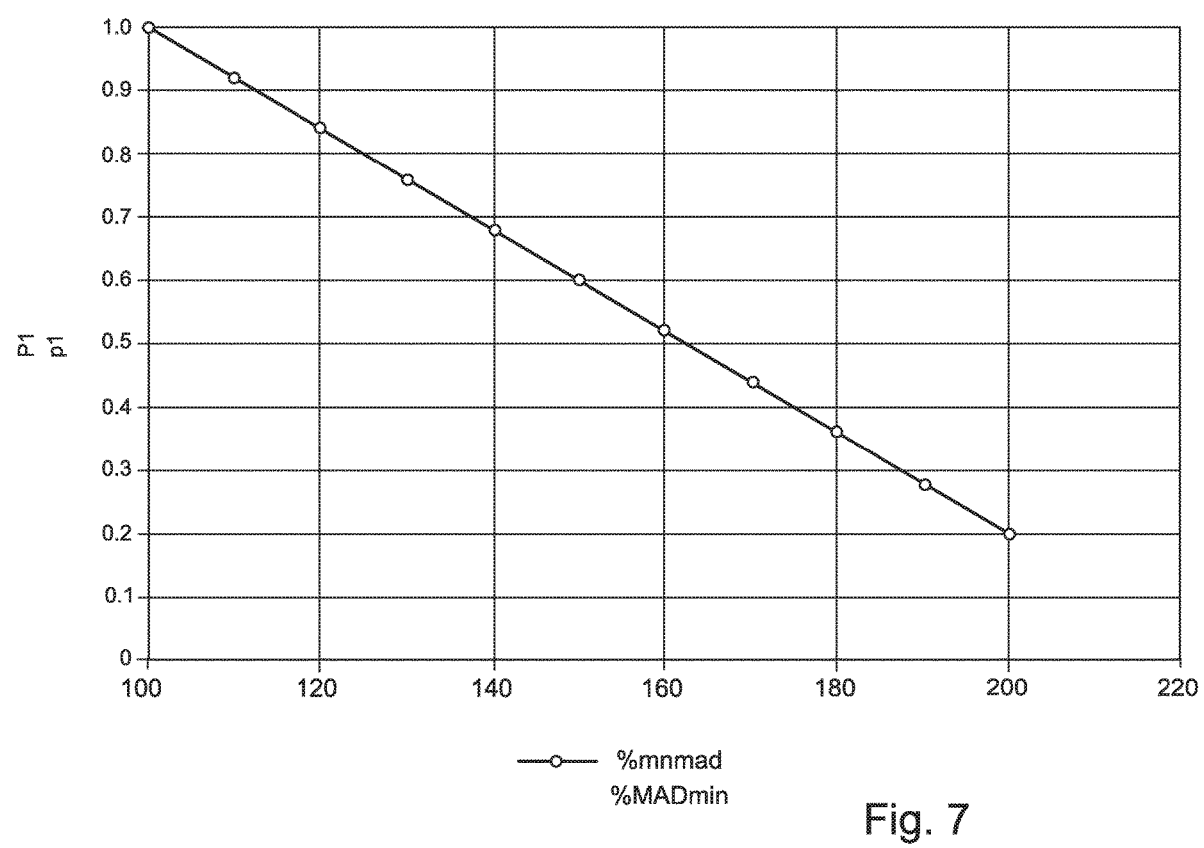
FIG. 7 presents an exemplary chart showing the effect of current MAD (as percentage of session's minimum MAD) on P1 value when current speed value remains constant.

In addition, AnT probably occurs in intensities where heart rate variability (=MAD) is close to a minimum value. P1 may decrease when the difference between current MAD and minimum MAD increases. FIG. 7 shows an example of the effect that current MAD (as a percentage of session's minimum MAD) may have on P1 value when current speed value is constant.

In further exemplary embodiments, the mathematical formula for P2 may be expressed as j=respective segment index, i runs here from 0 to j−1

$$\frac{\sum_{i=0}^{j-1}\left(\left(\frac{V_j - V_i}{(pHR_j - pHR_i)*maximalMET*1.5625} - 1\right)\Big/ MaxFunc\right)}{j}$$

where i runs from 0 to j−1 in each segment j and
maxFunc=1, if $(t_j-t_i)/5<1$, and
elsewhere maxFunc=$(t_j-t_i)/5$,
wherein $V_i$ is a user's stored speed in respective segment (or speed calculated from watts), $pHR_i$ is a user's stored heart rate relative to a maximal heart rate in respective segment and maximal MET is a user's maximal exercise capacity.

In the above formula for P2 the part $V_j-V_i$ may calculate the actual change in speed and $(pHR_j-pHR_i)*maximalMET*1.5625$ may describe how much a user's speed should increase relative to the increase in measured heart rate. As would be understood by a person of ordinary skill in the art, a user's maximal exercise capacity may influence this relationship. In addition, the gap in time between two moments may be taken into account to decrease its influence on P2 when the gap is increasing above five minutes, for example: M-code "max(1,abs($t(i)-t(1:i-1)$)/5)"

ie.
maxFunc=1, if $(t_j-t_i)/5<1$, and
elsewhere maxFunc=$(t_j-t_i)/5$,
Thus, and MaxFunc is a set limit function reducing the effect of those data points locating far in time scale from the new point.

Figure 8:
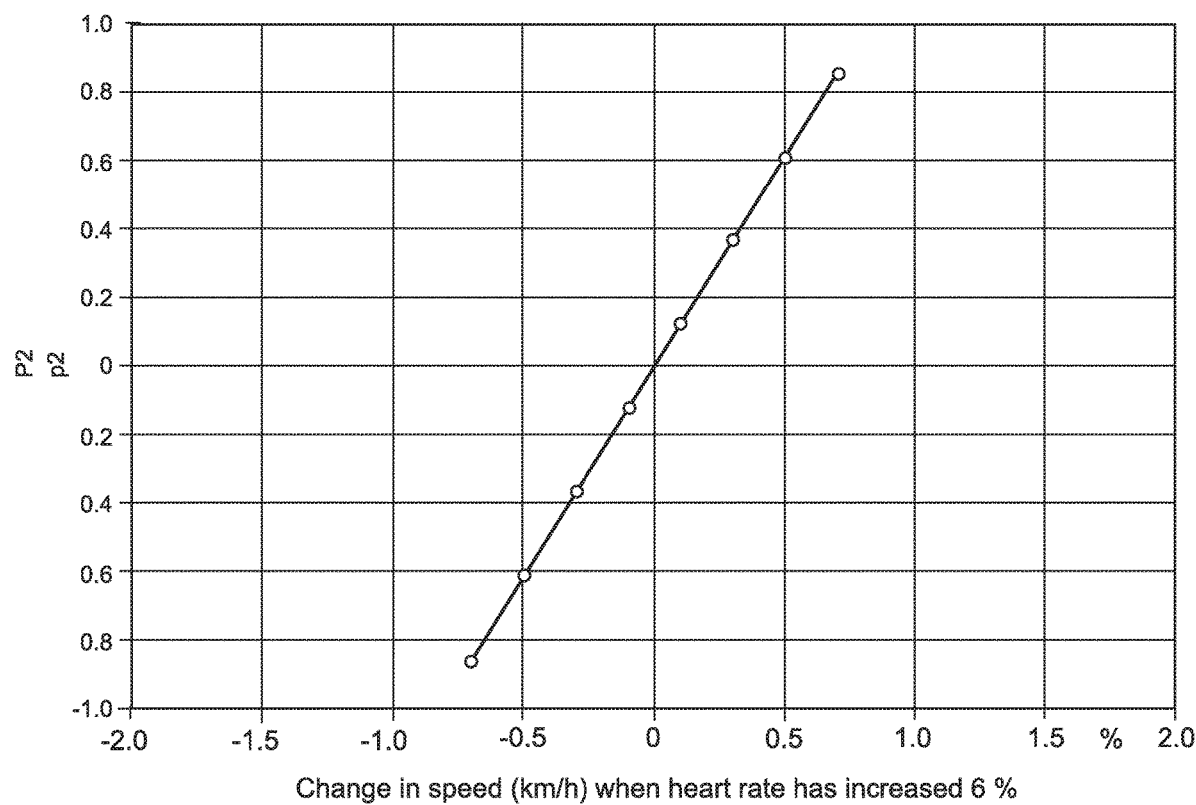
FIG. 8 presents an exemplary chart showing the effect of changing speed and heart rate on P2 value.
Figure 9:
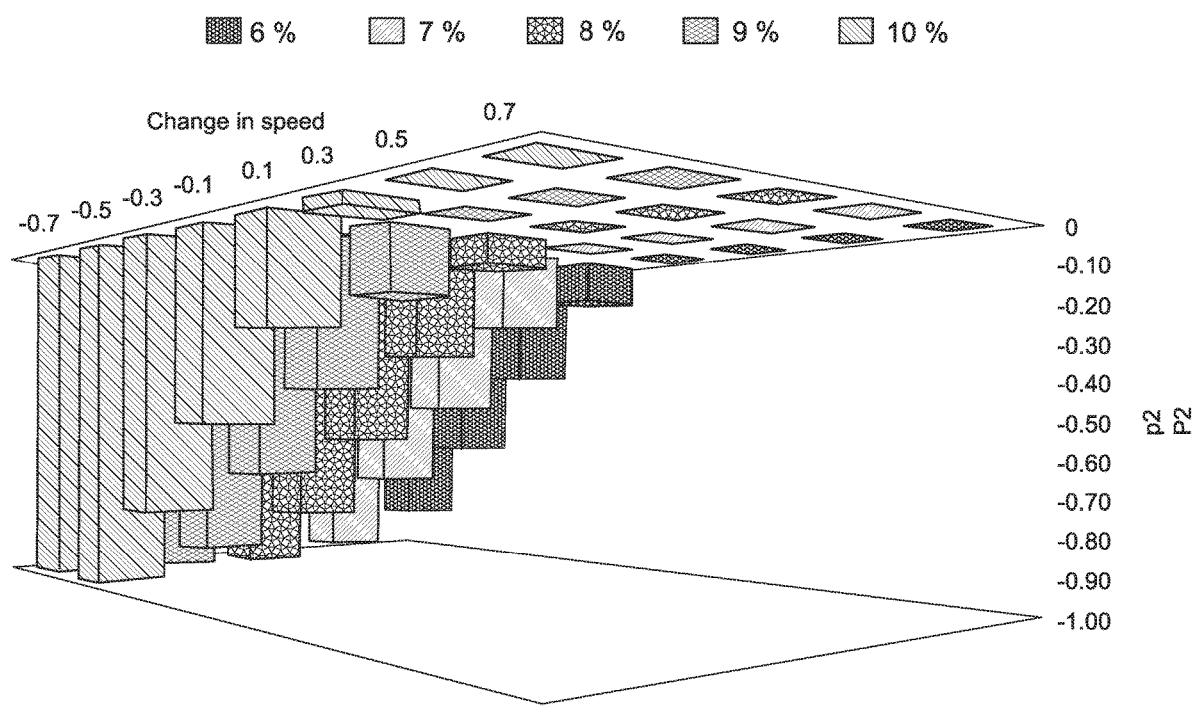
FIG. 9 presents an exemplary chart showing a changing relationship between speed and heart rate, and their consequent effect on P2 value.

The calculation of P2 may be used to decrease the AnT-probability of a measurement point, where heart rate may not stay in line with external workload (theoretical oxygen consumption, watts or speed). FIG. 8 shows an example of the effect that changing speed and heart rate may have on P2 value. In the example of FIG. 8, heart rate has increased 6% and the consequent change in speed may determine the P2 value. The value may only be taken into account if it is below 0. As would be understood by a person of ordinary skill in the art, in classic probability calculus, P-values cannot reach values below 0, but in fuzzy logics they may. FIG. 8 may represent just one exemplary case, and a broader example may be presented in FIG. 9 where more cases (heart rate increases between 6% and 10% and speed between −0.7 and +0.7 km/h) have been represented. Positive values have been excluded from exemplary FIG. 9. A person's maximum performance capacity (METmax or maxMET in this disclosure) may be one influencing factor. METmax value depends on personal physiological characteristics and training history. METmax typically varies between about 10-15 METs. The extent to which P2 value changes (due to heart rate vs. external workload relationship) may depend on a person's METmax-value. METmax value itself may be determined during the early phases of exercise as is disclosed in applicants's other patent applications (WO2015036651 and WO2012140322). Other options for determining METmax may comprise use of current and history exercises together, or METmax value may be set by the user before an exercise as a background parameter. In FIG. 8 and FIG. 9 an arbitrary value has been used for METmax and graphs may vary if lower or higher METmax value had been used.

In further exemplary embodiments, calculation of the probability may be expressed as Matlab® M-code:

$P3(i)=100*(101-phr(i))/11$, when $phr(i)>90\%$ $P3(i)=100*(11+phr(i)-90))/11$, when $phr(i)<=90\%$, wherein phr(i) is a user's stored heart rate in segment (i) proportional to the maximum heart rate of the user.

Figure 10:
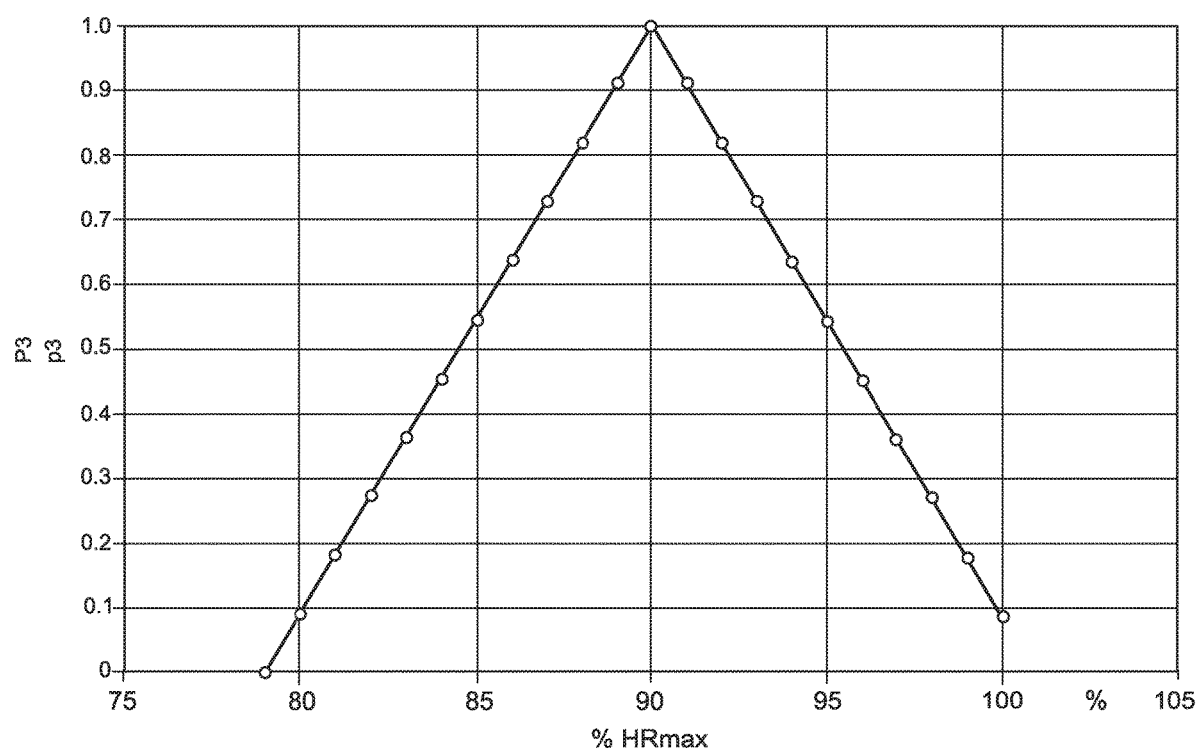
FIG. 10 presents an exemplary chart showing the effect of stored heart rate in respective segment (i) (% HRmax) on P3 value.

The calculation of P3 may be desired in that, according to empirical evidence AnT may occur at approximately 90% of maximal heart rate. Accordingly, the probability may decrease when intensity moves away from this intensity. FIG. 10 may show an example of the effect that stored heart rate in segment (i) (% HRmax) may have on P3 value.

In one exemplary embodiment, other signals—in addition to heart rate and external workload—may be measured and accompanied into the AnT estimation. One such signal is, for example, electromyographic (EMG) signal from muscles. EMG signal magnitude may provide one additional measure that could be taken into account in AnT estimation since there has been found AnT-induced non-linear change in EMG signal magnitude in incremental exercise tests. This threshold-like change may be associated to change in motor unit recruitment pattern when fast (type 2) muscle fibers are needed to be able to increase external workload. EMG-measuring pants are an example of a meaningful state-of-art method that could be incorporated to the exemplary embodiments in this document. Measured EMG-data could be transmitted to the CPU by using Bluetooth, for example.

State-of-art measurement methods may allow for integration of (transthoracic) bioimpedance recording equipment into a heart rate transmitter belt. In that case measurement of transthoracic impedance may allow a more detailed analysis of user's respiration rate and tidal volume, and consequently ventilation. These respiratory measures may increase the accuracy of AnT estimation when incorporated into the exemplary embodiments disclosed in this application.

It has been disclosed in this document that accuracy of the method may increase when more data is collected for a specific user by learning from the user data. When more measurement data is "fed" to the system, it is possible to use for example weighted average as a result to increase the robustness of the method. So if AnT-estimate heart rate on a previous day has been, for example 180, and on the day after it seems to be 174, then average value of 177 can be displayed to the user. One possible embodiment may also be to allow a user to set a measured AnT value as background parameter. Then this value could be used as one reference point in addition to actual estimates. It is also possible to weight AnT—estimates above regarding calculation of weighted average. More weight may be given for a reliable estimate: For example if there is a wide range of stored data regarding heart rate and number of segments. AnT estimates may be taken from different exercises on different days.

Figure 12:
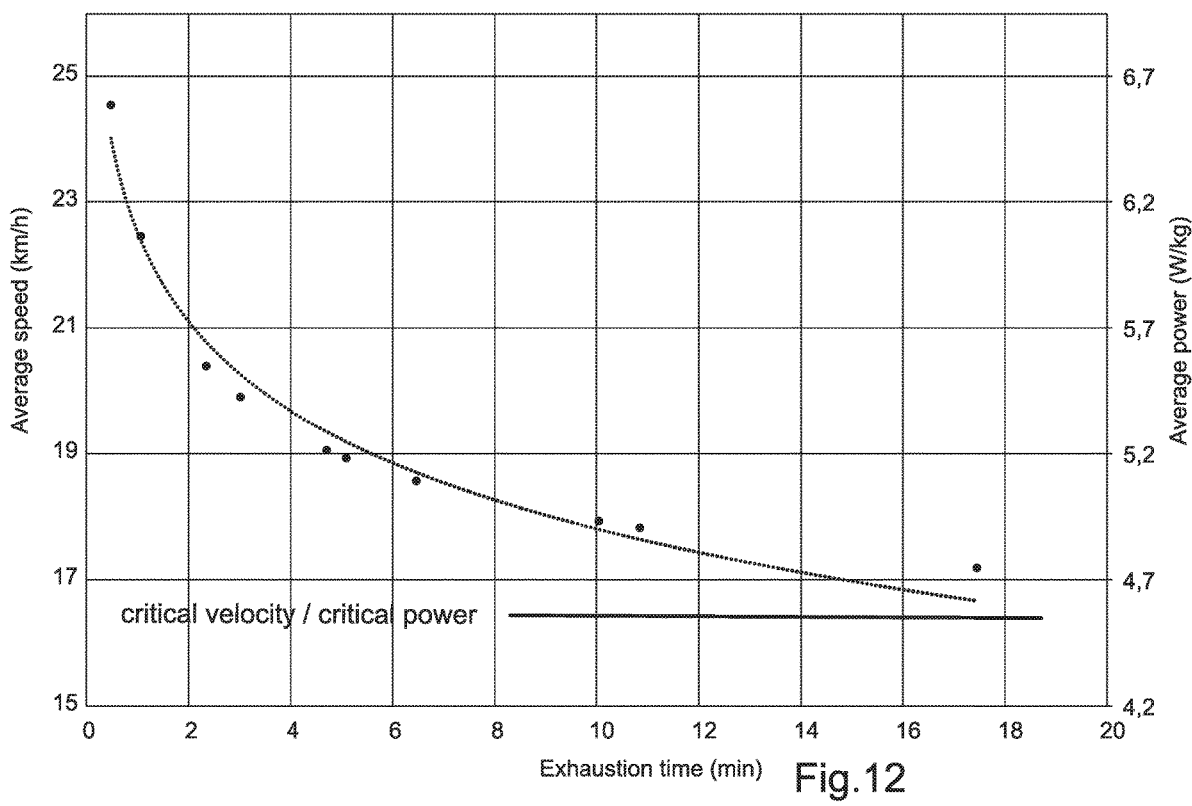
FIG. 12 presents an exemplary chart showing critical velocity and critical power.

There are also other ways to teach the system about a user's physiology: it may be possible to scan user data to find, for example, record times for different distances. Average speed (or theoretical VO2) can be observed in the case of running and average watts (per user's weight) in the case of cycling. Examples of this relationship may be shown in FIG. 12. Speed value and watt/kg value—where the line starts to level of—is called critical velocity or critical power. As mentioned earlier critical velocity/power correlates with AnT. By estimating critical velocity or critical power from history data it may be possible to increase accuracy of the AnT-estimate.

AnT may play an important role in training load and training effect assessment because training load may increase dramatically after intensity exceeds a person's AnT. Accordingly, more accurate AnT estimation as described in this disclosure can be utilized in many ways. In one exemplary embodiment, AnT may be used in calculation of training load (e.g. EPOC) and training effect during or after exercise.

In further exemplary embodiments, AnT may be utilized in training prescription. For example, a user can have a goal to improve marathon time. In that case, the user may desire to improve running speed corresponding to anaerobic threshold (v_ant), because a marathon race needs to be run without continuous lactate accumulation. As would be understood by a person of ordinary skill in the art, a basic rule of specificity of training (related to improvement of physiological or biomechanical characteristics) states that the intensity-range (speed range) most commonly used in training also improves the most. For example, marathon runners try to train as much as possible near AnT intensities, thereby trying to improve v_ant. Improvement of v_ant may be induced by, for example, improved running economy (lower oxygen cost of running), improved lactate removal, improved aerobic metabolism (improved fat metabolism), and the like. Due to more accurate AnT estimates, training prescription can be focused more accurately on AnT intensities, and consequently, v_ant can be improved more efficiently.

In some exemplary embodiments, a user may have a goal to improve performance in, for example, a 3 km or 5 km run, in a cooper (12 min) running test, or the like. In these embodiments, training of maximal oxygen uptake (VO2max) may be highly important. Because exercise intensities just above anaerobic threshold are very efficient in improving VO2max, it should be understood by a person of ordinary skill in art that the described embodiments can be efficiently utilized in a VO2max training prescription.

In still further exemplary embodiments the determined AnT may be utilized in selecting a target pace for a running or cycling race. For example, after a pace corresponding to AnT has been determined for a person, for example a target pace of 90% of that pace can be set for a marathon. Still further, the marathon target speed could be adjusted based on the fitness level of the user. For example, a target pace of 95% of v_ant may be set for a person with very high fitness level. The system and method according to the exemplary embodiments can be applied in many kinds of devices as would be understood by a person of ordinary skill in the art. For example, a wrist top device with a heart-rate transmitter, a mobile device such as a phone, tablet or the like, or other system having CPU, memory and software therein may be used.

Figure 11:
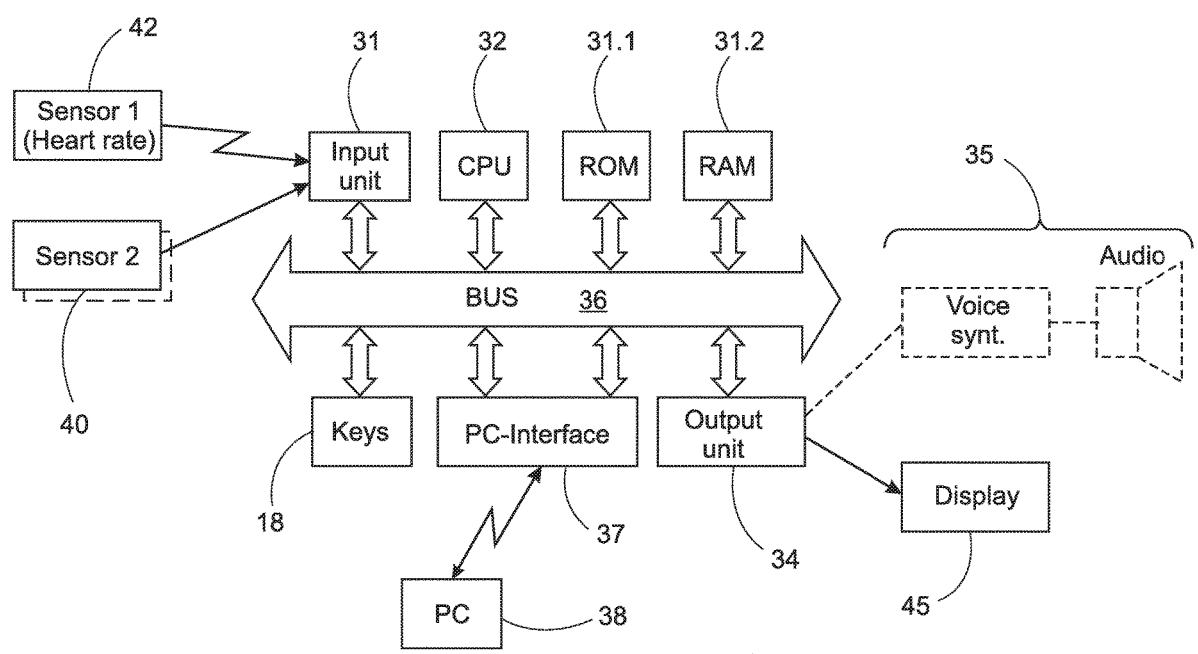
FIG. 11 presents an exemplary block diagram of a system with additional interfaces.

According to exemplary FIG. 11, in the implementation may include an assembly built around a central processing unit (CPU) 32. A bus 36 may transmit data between the central unit 32 and the other units. The input unit 31, ROM memory 31.1, RAM memory 31.2, keypad 18, PC connection 37, and output unit 34 may be connected to the bus.

The system may include a data logger which can be connected to cloud service, or other storage as would be understood by a person of ordinary skill in the art. The data logger may measure, for example, physiological response and/or external workload.

A heart rate sensor 42 and any sensor 40 registering external workload may be connected to the input unit 31, which may handle the sensor's data traffic to the bus 36. In some exemplary embodiments, the PC may be connected to a PC connection 37. The output device, for example a display 45 or the like, may be connected to output unit 34. In some embodiments, voice feedback may be created with the aid of, for example, a voice synthesizer and a loudspeaker 35, instead of, or in addition to the feedback on the display. The sensor 40 which may measure external workload may include any number of sensors, which may be used together to define the external work done by the user.

More specifically the system presented in FIG. 11 may have the following parts for determining a body's readiness to respond to physical exercise and provide feedback to a user:

a heart rate sensor 42 configured to measure the heartbeat of the person, the heart rate signal being representative of the heartbeat of the user;

at least one sensor (40) to measure an external workload during an exercise, and a data processing unit (32) operably coupled to the said sensors (42, 40), a memory (31.1, 31.2) operably coupled to the data processing unit (32), the memory may be configured to save background information of a user, for example, background data including an earlier performance level, user characteristics, and the like.

The data processing unit (32) may include dedicated software configured to execute the embodiments described in the present disclosure.

As described above in the exemplary embodiments, default values of the optional parameters (for example, P2 and P3) may be stored in a ROM memory, in an EEPROM (Electrically Erasable Programmable Read-Only Memory) memory, or in other memory as would be understood by a person of ordinary skill in the art.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

The invention claimed is:

1. A method for determining anaerobic threshold intensity (AnT) of a user in a freely performed physical exercise, comprising:

continuously measuring, by a body-mounted heart rate sensor, a physiological response of a user by heart rate, wherein a plurality of measured heart rate values are recorded with time stamps as heart rate data forming a recorded heart rate of the user;

continuously measuring an external workload in terms of speed and inclination or measured power, wherein a plurality of measured workload values are recorded and each measured workload value is associated with one of the plurality of measured heart rate values to form a plurality of data points;

calculating, by a processor, heart rate variability (HRV) values from intervals between successive heartbeats and storing each calculated HRV value associating to a data point;

filtering, by the processor, one or more data points based on a predetermined criteria to form a plurality of accepted data points;

classifying, by the processor, accepted data points within a plurality of heart rate segments (i) representing a heart rate within an anaerobic threshold (AnT) of the user, wherein at least one segment is below a probable heart rate value of AnT, and at least one segment is above the probable heart rate value of AnT;

calculating, by the processor, a first probability factor (P1) for each of the plurality of accepted data points based on the measured external workload value and a calculated heart rate variability value of each data point;

comparing, by the processor, the calculated first probability factor with at least one stored probability factor in a respective segment, and if the first probability factor is higher than the at least one stored probability factor, the stored probability factor is updated by the first probability factor;

determining if a second probability factor (P2) needs to be created or updated, and calculating, by the processor, the second probability factor of each stored data point for each respective segment based on a deviation between change in recorded external workload and expected change in external workload;

determining if a third probability factor (P3) needs to be created or updated, and calculating, by the processor, the third probability factor of each stored data point for each respective segment based on the recorded heart rate of the user in proportion to the maximum heart rate of the user;

calculating, by the processor, a total probability (P) of each recorded heart rate in each segment using the first probability factor, the second probability factor, and the third probability factor wherein the total probability is derived from a sum of the first probability factor, the second probability factor, and the third probability factor, the sum being raised by the power of a constant;

calculating, by the processor, an estimate of the user's AnT as a weighted value of heart rate values recorded for each segment, wherein each recorded heart rate value in each segment is multiplied by the total probability stored for that segment when all weighted values are added together; and outputting, to an output device, the estimate of the user's AnT.

2. The method of claim 1, wherein the first probability factor is calculated based on a first relationship between current measured external workload and highest measured external workload, and a second relationship between current measured heart rate variability level and lowest measured heart rate variability level; and wherein the method further comprises:

generating and maintaining an index-based register, and storing, in the index-based register, the plurality of heart rate segments (i); and associating, in the index-based register, at a first index value, a particular heart rate segment (i) and the first probability factor following, in real-time, the measurement of the particular heart rate segment (i).

3. The method of claim 2, wherein the first probability factor (P1) is calculated according to the equation:

$$P1 = (1500 - 100*(v\max - v) - 600*(MAD - MAD\min))/15,$$

wherein v=current measured external workload as at least one of current speed or velocity or power output, vmax=highest measured external workload as at least one of the highest speed or velocity or power output, MAD=current measured heart rate variability level, and MADmin=lowest measured heart rate variability level.

4. The method of claim 1, wherein the second probability factor and the third probability factor are based on population reference values.

5. The method of claim 1, wherein the second probability factor (P2) for a particular heart rate segment (i) is calculated according to the equation:

$$\frac{\sum_{i=0}^{j-1}\left(\left(\frac{V_j - V_i}{(pHR_j - pHR_i)*maximalMET*1.5625}\right) - 1\right) / MaxFunc}{(j)}$$

wherein j is a respective segment index, i runs from 0 to j, $V_i$ is a user's recorded external workload in segment (i), $pHR_i$ is a user's recorded heart rate in segment (i) relative to a maximum heart rate, and maximal MET is a user's maximal exercise capacity, and MaxFunc is a set limit function reducing the effect of old datapoints.

6. The method of claim 1, wherein the third probability factor (P3) is calculated according to the equation:

$P3(i)=100*(101-phr(i))/11$, when $phr(i)$ is greater than 90%; or $P3(i)=100*(11+phr(i)-90)/11$ when $phr(i)$ is less than or equal to 90%;

wherein phr(i) is a user's recorded heart rate proportional to the maximum heart rate of the user in segment (i).

7. The method of claim 1, wherein the estimate of the user's AnT as a weighted value of the recorded heart rates (HR) of each segment (i) is calculated according to the equation:

$$AnT(t) = \frac{\sum (HR[i] * (P[i]^y)}{\sum (P[i]^y)}$$

wherein P[i] is the total probability of each segment (i), and y is a chosen power value.

8. The method of claim 1, wherein the estimate of the user's AnT can be displayed to the user during the exercise or after the exercise.

9. The method of claim 1, wherein the estimate of the user's AnT can be displayed to the user as a value describing external workload.

10. The method of claim 1, wherein the plurality of heart rate segments include 5-30 segments.

11. The method of claim 10, wherein the size of each segment is 0.5-3% of the user's maximum heart rate.

12. A system for determining anaerobic threshold intensity (AnT) of a user in a freely performed physical exercise, comprising:
means for continuously measuring a physiological response of a user by heart rate, said means disposed on the body of the user, wherein a plurality of measured heart rate values are recorded with time stamps as heart rate data forming a recorded heart rate of the user;
means for continuously measuring an external workload in terms of speed and inclination or measured power, wherein a plurality of measured workload values are recorded and each measured workload value is associated with one of the plurality of measured heart rate values to form a plurality of data points;
means for calculating heart rate variability (HRV) values from intervals between successive heartbeats and storing each calculated HRV value associating to a data point;
means for filtering one or more data points based on a predetermined criteria to form a plurality of accepted data points;
means for classifying accepted data points within a plurality of heart rate segments (i) representing a heart rate within an anaerobic threshold (AnT) of the user, wherein at least one segment is below a probable heart rate value of AnT, and at least one segment is above the probable heart rate value of AnT,
means for calculating a first probability factor (P1) for each of the plurality of accepted data points based on the measured external workload value and a calculated heart rate variability value of each data point;
means for comparing the calculated first probability factor with at least one stored probability factor in a respective segment, and if the first probability factor is higher than the at least one stored probability factor, the stored probability factor is updated by the probability factor;
means for determining whether a second probability factor (P2) needs to be created or updated, and for calculating the second probability factor of each stored data point for each respective segment based on a deviation between change in recorded external workload and expected change in external workload;
means for determining whether a third probability factor (P3) needs to be created or updated, and for calculating the third probability factor of each stored data point for each respective segment based on the recorded heart rate of the user in proportion to the maximum heart rate of the user;
means for calculating a total probability (P) of each recorded heart rate in each segment using the first probability factor, the second probability factor, and the third probability factor wherein the total probability is derived from a sum of the first probability factor, the second probability factor, and the third probability factor, the sum being raised by the power of a constant;
means for calculating an estimate of the user's AnT as a weighted value of heart rate values recorded for each segment, wherein each recorded heart rate value in each segment is multiplied by the total probability stored for that segment when all weighted values are added together;
means for outputting the estimate of the user's AnT to an output device.

13. The system of claim 12, wherein the second probability factor and the third probability factor are only calculated when the estimate of the user's AnT is required.

14. The system of claim 12, wherein the first probability factor is calculated based on a first relationship between current measured external workload and highest measured external workload, and a second relationship between current measured heart rate variability and lowest measured heart rate variability level.

15. The system of claim 12, wherein the estimate of the user's AnT can be displayed to the user during the exercise or after the exercise.

16. The system of claim 12, wherein the plurality of heart rate segments include between 5-30 consecutive 0.5-3% segments of the maximum heart rate of the user.

17. A method for determining anaerobic threshold intensity (AnT) of a user in a freely performed physical exercise, comprising:
continuously measuring, by a body-mounted heart rate sensor, a physiological response of a user by heart rate, wherein a plurality of measured heart rate values are recorded with time stamps as heart rate data forming a recorded heart rate of the user;
continuously measuring an external workload in terms of speed and inclination or measured power, wherein a plurality of measured workload values are recorded and each measured workload value is associated with one of the plurality of measured heart rate values to form a plurality of data points;
calculating, by a processor, heart rate variability (HRV) values from intervals between successive heartbeats and storing each calculated heart rate variability value associating to a data point;
filtering, by a processor, one or more data points based on a predetermined criteria to form a plurality of accepted data points;
classifying, by a processor, accepted data points within a plurality of heart rate segments (i) representing a heart rate within an anaerobic threshold (AnT) of the user, wherein at least one segment is below a probable heart rate value of AnT, and at least one segment is above the probable heart rate value of AnT, wherein a data point with highest probability is stored for each segment;

calculating, by a processor, a first probability factor (P1) for each of the plurality of accepted data points based on at least the measured external workload value and a calculated heart rate variability value of each data point;

retrieving, by the processor, from a set of stored probability data, at least one stored probability factor for a respective segment, the set of stored probability data further comprising a second probability factor (P2) and a third probability factor (P3);

comparing, by a processor, the calculated first probability factor with the at least one stored probability factor in the respective segment, and if the first probability factor is higher than the at least one stored probability factor, the stored probability factor is updated by the first probability factor, and at least one further calculation is triggered to update stored probability data other than with the first probability factor; and calculating, by a processor, AnT using the stored probabilities in each segment; and outputting, to an output device, the estimate of the user's AnT to an output device.

18. The method of claim 17, further comprising:
triggering a calculation of the at least one second probability factor (P2) based on chosen parameters of said data point if the first probability factor replaces the at least one stored probability factor;

calculating a total probability of each recorded heart rate in each segment using the first probability factor and the at least one second probability factor;

calculating an estimate of the user's AnT as a weighted value of heart rate value recorded for each segment, wherein each recorded heart rate value in each segment is multiplied by the total probability of that segment when all weighted values are added together.

19. The method of claim 18, wherein at least one second probability factor is only calculated when the estimate of the user's AnT is required.

20. The method of claim 17, wherein the first probability factor is calculated based on a first relationship between current external workload and highest measured external workload, and a second relationship between current and lowest measured heart rate variability level.

21. The method of claim 17, wherein the first probability factor (P1) is calculated according to the equation:

wherein v=current measured external workload as at least one of current speed or velocity or power output, vmax=highest measured external workload as at least one of the highest speed or velocity or power output, MAD=current measured heart rate variability level, and MADmin=lowest measured heart rate variability level.

22. The method of claim 21, wherein the estimate of the user's AnT as a weighted value of the highest recorded heart rates (HR) of each segment (i) is calculated according to the equation:

$$AnT(t) = \frac{\sum (HR[i] * (P[i]^y))}{\sum (P[i]^y)}$$

wherein P[i] is the total probability of each segment (i) and y is a chosen power value.

23. The method of claim 17, wherein the at least one second probability factor is based on population reference values.

24. The method of claim 23, wherein the population reference values are based on a population average of heart rate level corresponding to AnT.

25. The method of claim 23, wherein the population reference values are based on a population average of heart rate level corresponding to AnT.

26. The method of claim 23, wherein the population reference values are based on a linear dependency between heart rate and external workload.

27. The method of claim 17, wherein the plurality of heart rate segments includes 5-30 segments.

28. The method of claim 27, wherein a size of each segment is 0.5-3% of the user's maximum heart rate.

29. The method of claim 17, wherein a final AnT estimate is calculated from at least two AnT estimates weighted by a chosen criteria.

30. The method of claim 17, wherein an AnT estimate is given to a user only if exercise heart rate reaches a chosen limit.

* * * * *